United States Patent
Schmidt et al.

(10) Patent No.: US 9,630,892 B2
(45) Date of Patent: *Apr. 25, 2017

(54) METHOD FOR CONVERTING HYDROCARBON FEEDSTOCKS BY MEANS OF THERMAL STEAM CRACKING

(71) Applicant: Linde Aktiengesellschaft, Munich (DE)

(72) Inventors: Gunther Schmidt, Deisenhofen (DE); Stefanie Walter, Seehausen (DE); Helmut Fritz, Munich (DE)

(73) Assignee: Linde Aktiengesellschaft, München (DE)

(*) Notice: Subject to any disclaimer, the term of this patent is extended or adjusted under 35 U.S.C. 154(b) by 48 days.

This patent is subject to a terminal disclaimer.

(21) Appl. No.: 14/420,643

(22) PCT Filed: Aug. 1, 2013

(86) PCT No.: PCT/EP2013/002295
§ 371 (c)(1),
(2) Date: Feb. 9, 2015

(87) PCT Pub. No.: WO2014/023406
PCT Pub. Date: Feb. 13, 2014

(65) Prior Publication Data
US 2015/0307417 A1 Oct. 29, 2015

(30) Foreign Application Priority Data
Aug. 9, 2012 (EP) .................... 12005780

(51) Int. Cl.
*C07C 4/04* (2006.01)
*C10G 9/36* (2006.01)
(52) U.S. Cl.
CPC .............. *C07C 4/04* (2013.01); *C10G 9/36* (2013.01); *C10G 2400/20* (2013.01)

(58) Field of Classification Search
None
See application file for complete search history.

(56) References Cited

U.S. PATENT DOCUMENTS

| | | |
|---|---|---|
| 2004/0209964 A1 | 10/2004 | Ansorge et al. |
| 2008/0194900 A1 | 8/2008 | Bhirud |
| 2008/0223754 A1 | 9/2008 | Subramanian et al. |

FOREIGN PATENT DOCUMENTS

| | | |
|---|---|---|
| CN | 1665911 A | 9/2005 |
| FR | 1196927 A | 11/1959 |

(Continued)

OTHER PUBLICATIONS

Chinese application No. 201380040778.9, English Translation of First Office Action dated Jan. 26, 2016, 11 pages.

(Continued)

*Primary Examiner* — Tam M Nguyen
(74) *Attorney, Agent, or Firm* — Lathrop & Gage LLP

(57) ABSTRACT

The invention relates to a process for converting hydrocarbon feeds by thermal steamcracking to at least one olefin-containing product stream comprising at least ethylene and propylene, with at least partial conversion of a first hydrocarbon feed in at least one first cracking furnace (1) and of a second hydrocarbon feed in at least one second cracking furnace (2). According to the invention, the second hydrocarbon feed comprises predominantly hydrocarbons having a carbon number of 5 or/and 4 and consists for the most part of one or more recycled fractions (P, T) which are obtained from the product stream, and the second hydrocarbon is converted in the second cracking furnace (2) with cracking conditions that lead to a ratio of propylene to ethylene of 0.7 to 1.6 kg/kg.

13 Claims, 2 Drawing Sheets

(56) References Cited

FOREIGN PATENT DOCUMENTS

GB          1357495  A      6/1974
WO       03099964  A1    12/2003

OTHER PUBLICATIONS

PCT/EP2013/002295 English Translation of the International Preliminary Report on Patentability mailed Dec. 4, 2014, 7 pages.
PCT/EP2013/002295 English Translation of the International Search Report mailed Oct. 22, 2013, 3 pages.
Translation of the Decision to Grant corresponding to patent application No. 2015/0248.1 in Kazakhstan, received Nov. 24, 2016, 5 pages.
English translation of comments in Notice of Office Action corresponding to Egyptian Patent Application with priority filed under No. 2090/2014 based on PCT/EP2013/002295, dated Oct. 5, 2016, 1 page.

METHOD FOR CONVERTING HYDROCARBON FEEDSTOCKS BY MEANS OF THERMAL STEAM CRACKING

The present invention relates to a process for converting hydrocarbon feeds by thermal steamcracking to at least one olefin-containing product stream comprising at least ethylene and propylene, with at least partial conversion of a first hydrocarbon feed in at least one first cracking furnace and of a second hydrocarbon feed in at least one second cracking furnace.

Thermal steamcracking is a long-established petrochemical process. The standard target compound in thermal steamcracking is ethylene (also referred to as ethene), which is an important starting compound for a number of chemical syntheses.

The feeds used for the thermal steamcracking may be either gases such as ethane, propane or butane and corresponding mixtures or liquid hydrocarbons, for example naphtha, and hydrocarbon mixtures.

With regard to the specific apparatuses and reaction conditions used in thermal steamcracking, and with regard to the reactions which proceed and to details of refinery technology, reference is made to corresponding articles in reference works such as Zimmermann, H. and Walzl, R.: Ethylene, in: Ullmann's Encyclopedia of Industrial Chemistry. 6th ed. Weinheim: Wiley-VCH, 2005, and Irion, W. W. and Neuwirth, O. S.: Oil Refining, in: Ullmann's Encyclopedia of Industrial Chemistry. 6th ed. Weinheim: Wiley-VCH 2005. Processes for producing olefins are also disclosed, for example, in U.S. Pat. No. 3,714,282 A and U.S. Pat. No. 6,743,961 B1. U.S. 2008/0223754 discloses, for example, that crackers, for example hydrocrackers, catalytic crackers, FCC crackers or thermal steamcrackers can be used in refineries for processing operations on hydrocarbon cuts.

For thermal steamcracking, cracking furnaces are used. The cracking furnaces, together with a quench unit and downstream devices for processing of the product mixtures formed, are integrated into corresponding larger plants for olefin production, which are referred to in the context of this application as "steamcrackers".

An important parameter in thermal steamcracking is the so-called cracking severity, which determines the cracking conditions. The cracking conditions are influenced especially by the temperature and residence time and the partial pressures of the hydrocarbons and of the steam. The composition of the hydrocarbon mixtures used as the feed and the design of the cracking furnaces used also influence the cracking conditions. Because of the mutual influences of these factors, the cracking condition is normally defined via the ratio of propylene (also referred to as propene) to ethylene in the cracking gas.

According to the feed mixture and cracking conditions, thermal steamcracking gives rise not only to ethylene, the conventional target compound, but also to sometimes considerable amounts of by-products, which can be separated from a corresponding product stream. These include lower alkenes, for example propylene and butenes, and also dienes, for example butadienes, and also aromatics, for example benzene, toluene and xylenes. These are of comparatively high economic value, and so the formation thereof as "high-value products" is desirable.

The problem addressed by the present invention is therefore that of improving the means of obtaining olefin-containing product mixtures from hydrocarbons by thermal steamcracking.

DISCLOSURE OF THE INVENTION

Against this background, the invention proposes a process for converting hydrocarbon feeds by thermal steamcracking to at least one olefin-containing product stream comprising at least ethylene and propylene, with at least partial conversion of a first hydrocarbon feed in at least one first cracking furnace and of a second hydrocarbon feed in at least one second cracking furnace, having the features of the independent claims. Preferred configurations are the subject of the dependent claims and of the description which follows.

ADVANTAGES OF THE INVENTION

According to the invention, a process is proposed in which the second hydrocarbon feed comprises predominantly hydrocarbons having a carbon number of 5 or/and 4 and consists for the most part of one or more recycled fractions which are obtained from the product stream, the second hydrocarbon being converted in the second cracking furnace (2) with cracking conditions that lead to a ratio of propylene to ethylene of 0.7 to 1.6 kg/kg.

In the context of the invention, the first and second hydrocarbon feeds refer to all hydrocarbons which are conducted into the first and second cracking furnaces respectively. Thus, a first hydrocarbon feed is at least partly converted in a first cracking furnace, and a second hydrocarbon feed in a second cracking furnace. According to the invention, the second hydrocarbon feed advantageously consists of one fraction or of several fractions which are separated from the product stream and recycled into the second cracking furnace, in which the second hydrocarbon feed is converted at the second cracking severity. It is thus advantageous not to add any fresh feed to the second hydrocarbon feed, and it is also advantageous not to supply any fresh feed to the second cracking furnace either.

A cracking furnace is understood in the context of this invention to mean a cracking unit in which the cracking conditions are defined. It is possible that a subdivision into two or more cracking furnaces is present in one overall furnace. In that case, reference is frequently made to furnace cells. A plurality of furnace cells forming part of an overall furnace generally have independent radiation zones and a common convection zone, and also a common smoke outlet. In these cases, each furnace cell can be operated with its own cracking conditions. Each furnace cell is thus a cracking unit and is consequently referred to here as a cracking furnace. In that case, the overall furnace has a plurality of cracking units or, in other words, it has a plurality of cracking furnaces. If only one furnace cell is present, this is the cracking unit and hence the cracking furnace. Cracking furnaces can be combined to form groups, which are supplied, for example, with the same feed. The cracking conditions within a furnace group are generally the same or similar.

Since the second hydrocarbon feed, in accordance with the invention, consists for the most part of recycled fractions, the composition of the second hydrocarbon feed is well-defined. This is especially true compared to hydrocarbon feeds comprising a fresh feed. The second hydrocarbon is then converted in the at least one second cracking furnace. This has the advantage that cracking conditions and feed can be optimized with respect to one another. If the second hydrocarbon feed consists of predominantly hydrocarbons having a carbon number of 5 or/and 4, it can be cracked under mild and very mild conditions.

In contrast, the thermal cracking of hydrocarbons of typical composition, for example naphtha, under mild cracking conditions gives rise to very large amounts of pyrolysis gasoline, which is very difficult to deal with because of the large amount. This is a result of the comparatively lower conversion of the feed in the cracking furnace under mild cracking conditions. The achievement of the process according to the invention is that these problems do not occur.

The process according to the invention thus makes it possible to operate a steamcracking plant in such a way that more propylene is formed in relation to the fresh feed than in a conventional plant in which the process according to the invention is not used. Thus, there is an increase in the yield of propylene. This is achieved by the invention, more particularly, by virtue of cracking being performable advantageously under mild cracking conditions through the selective recycling of fractions.

The word "predominantly" is used in the context of this application to make it clear that the feed or the fraction does not consist exclusively of hydrocarbons having the specified carbon number, but that hydrocarbons having other carbon numbers and other impurities may also be present alongside the hydrocarbons of the specified carbon number. The separation and processing of the product stream and/or the fractions always leaves residues of the component(s) in the product stream or in the fraction. Other impurities also persist, and so a processed product stream or fraction stream always contains residues. Since the cost and inconvenience associated with separation and processing rise to an extremely high degree with the purity to be achieved, economic factors decide what proportion of residues may be present in a stream that is withdrawn in order to recycle it, for example. The level of this proportion has to be weighed up according to economic considerations. A rough guide value for the proportion of unwanted hydrocarbons and other impurities will generally be that not more than 30 to 40 percent by weight may be present in the product stream and/or in the fraction. Usually, a maximum value of 15 percent by weight or less is actually attained. For the recycled fractions, therefore, it is generally the case that they contain the desired hydrocarbons at at least 60 percent by weight, preferably at least 80 percent by weight and further preferably at least 90 percent by weight and more preferably at least 95 percent by weight and most preferably at least 98 percent by weight.

The feature that the second hydrocarbon feed consists for the most part of one or more recycled fractions which are separated from the product stream means that the recycled fraction(s) make(s) up the majority of the second hydrocarbon feed. In principle, however, addition of a fresh feed or of other recycled fractions is possible, provided that such an addition is only of minor importance; in other words, the characteristics of the second hydrocarbon are determined essentially by the properties of recycled fractions according to claim 1. How large any further proportion in the second hydrocarbon feed may be consequently also depends on the extent to which the properties of this proportion that may additionally be added differ from the properties of the recycled fractions according to claim 1. A guide value is, however, that the recycled fractions according to claim 1 predominate at a level of more than half and preferably make up more than three quarters of the second hydrocarbon feed, more preferably more than 90 percent and most preferably more than 95 percent of the second hydrocarbon feed. More particularly, the second hydrocarbon stream consists exclusively of one or more recycled fractions which are obtained from the cracking product streams.

The procedures which are needed to obtain the second hydrocarbon feed are known to those skilled in the art. These are measures customary in steamcrackers for separation and processing of product and fraction streams.

The advantages of the invention are manifested when the second hydrocarbon feed comprises predominantly hydrocarbons having a carbon number of 5 or/and 4. The second hydrocarbon feed may thus comprise predominantly hydrocarbons having a carbon number of 5 or hydrocarbons having a carbon number of 4 or mixtures of hydrocarbons having carbon numbers of 5 and of 4. In many applications, the mixtures of hydrocarbons having carbon numbers of 5 and 4 are particularly advantageous as the second hydrocarbon.

Particularly advantageously, the second hydrocarbon feed comprises predominantly saturated hydrocarbons. The use of predominantly saturated hydrocarbons as the second hydrocarbon feed improves the thermal steamcracking and gives rise to a high proportion of products of value. This rise in the level of products of value is manifested particularly in the second hydrocarbon feed because its carbon number is fixed in claim 1.

In order that it is possible to use predominantly saturated hydrocarbons as the feed, the recycling must be preceded by a saturation. This can be used to saturate only the fractions which are recycled into the second hydrocarbon feed, or saturation can already be effected at any point upstream of the separation of these fractions. The methods for separation and for saturation are known to those skilled in the art and are typically used in steamcrackers.

In an advantageous configuration of the invention, the second hydrocarbon is substantially free of diolefins. Diolefins have disadvantageous effects in a cracking furnace. For this purpose, the diolefins are predominantly removed by upstream conversion processes or separation steps from the fractions which are recycled into the second cracking furnace. The removal may either precede or follow the separation of the fractions which are recycled into the second cracking furnace.

More particularly, it is advantageous when the hydrocarbons having a carbon number of 5 present in the second hydrocarbon feed are predominantly saturated hydrocarbons. It is advantageous to use such an feed for operation of the second cracking furnace. More particularly, such an feed is of particularly good suitability for cracking under mild conditions.

For the first hydrocarbon feed, the customary feeds are used (see page 1), for which the cracking conditions of the first cracking furnace are of very good suitability. More particularly, the first cracking furnace is suitable for converting long-chain hydrocarbons. Advantageously, hydrocarbons having a carbon number of 6 or more are therefore also recycled into the first cracking furnace. Thus, the first hydrocarbon feed advantageously comprises at least one fraction which has been separated from the product stream and recycled, and which comprises predominantly hydrocarbons having a carbon number of at least 6.

According to the invention, the second hydrocarbon is converted in the second cracking furnace with cracking conditions that lead to a ratio of propylene to ethylene of 0.7 to 1.6 kg/kg. Preferably, the second hydrocarbon is converted in the second cracking furnace with cracking conditions that lead to a ratio of propylene to ethylene of 0.8 to 1.4 kg/kg, more preferably of 0.85 to 1.2 kg/kg, at the cracking furnace outlet. If the feed is converted under mild cracking conditions, the aforementioned advantages of the invention are manifested particularly markedly. Also advantageous are cracking conditions that lead to a ratio of propylene to ethylene at the cracking furnace outlet of 0.75 to 1.5 kg/kg or of 0.8 to 1.2 kg/kg or of 0.85 to 1.15 kg/kg, or which are even within the narrow range of 0.9 to 1.1 kg/kg.

It is additionally advantageous when the first hydrocarbon feed is converted with cracking conditions that lead to a ratio of propylene to ethylene of 0.25 to 0.85 kg/kg, preferably of 0.3 to 0.75 kg/kg, likewise preferably of 0.35 to 0.7 kg/kg, more preferably of 0.4 to 0.65 kg/kg, at the cracking furnace outlet, the value for the ratio of propylene to ethylene for the second hydrocarbon feed being above the value for the ratio of propylene to ethylene for the first hydrocarbon feed.

The operation of at least two cracking furnaces under the various cracking conditions just specified achieves very particular advantages, since the cracking conditions in the two cracking furnaces can be matched to the respective feed. For instance, it is a feature of the second hydrocarbon feed that it can be used to achieve the very high values specified for the ratio of propylene to ethylene. The first hydrocarbon feed, in contrast, is converted under standard cracking conditions. The matching of the cracking conditions to the first and second hydrocarbon feeds achieves the effect that the pyrolysis gasoline fraction remains controllable in terms of amount. The second hydrocarbon feed too, under mild conditions, forms smaller amounts of pyrolysis oil than the first hydrocarbon feed. For the thermal steamcracking under the first cracking conditions in the first cracking furnace, in contrast, a standard feed which forms controllable amounts of pyrolysis gasoline under standard cracking conditions is used.

In this context, the values for the ratio of propylene to ethylene for the first and second hydrocarbons advantageously differ by at least 0.1 kg/kg, preferably by at least 0.15 kg/kg and more preferably by at least 0.2 kg/kg.

As explained at the outset, the ratio of propylene to ethylene in the thermal steamcracking operation results from a number of different influencing factors, among which the cracking furnace exit temperature, i.e. the temperature of a product stream on leaving the reactor coil used (coil output temperature), plays an important role. The cracking furnace exit temperature for the conversion in the second cracking furnace is advantageously between 680° C. and 820° C., preferably between 700° C. and 800° C. and further preferably between 710° C. and 780° C. and more preferably between 720° C. and 760° C. The cracking furnace exit temperature for the conversion in the first cracking furnace is advantageously between 800° C. and 1000° C., preferably between 820° C. and 950° C. and more preferably between 840° C. and 900° C. The cracking furnace exit temperature in the first cracking furnace is always higher than in the second cracking furnace.

The cracking furnace exit temperature for the conversion in the first cracking furnace is preferably at least 10° C. above, more preferably at least 15° C. above and most preferably at least 20° C. above the cracking furnace exit temperature for the conversion in the second cracking furnace.

In the second cracking furnace, a lower steam dilution than in the first can also be used. This reduces the amount of dilution steam needed and saves energy. However, a lower steam dilution in the second cracking furnace is unnecessary for the significant advantages of the invention to be manifested. Advantageously, in the second cracking furnace 0.15 to 0.8 kg of steam per kg of hydrocarbon is used in the feed, whereas in the first cracking furnace 0.3 to 1.5 kg of steam per kg of hydrocarbon is used in the feed.

It is also advantageously possible to convert especially saturated hydrocarbons having a carbon number of 2 to 3 present in the product stream advantageously by means of thermal steamcracking in a cracking furnace for gaseous feed. To this end, the saturated gaseous hydrocarbons are obtained from the product stream, and recycled into and converted in the cracking furnace for gaseous feed.

The fresh feeds used for the first hydrocarbon feed may be either gases or gas fractions, such as ethane, propane or butane, and corresponding mixtures and condensates, or liquid hydrocarbons and hydrocarbon mixtures. These gas mixtures and condensates comprise especially what are called natural gas condensates (natural gas liquids, NGL). The liquid hydrocarbons and hydrocarbon mixtures may originate, for example, from what is called the gasoline fraction of crude oil. Such crude gasolines or naphthas (NT) and kerosene are mixtures of preferably saturated compounds having boiling points between 35 and 210° C. However, the invention is also advantageous in the case of use of middle distillates, atmospheric residues and/or mixtures derived therefrom from crude oil processing. Middle distillates comprise what are called light and heavy gas oils which can be used as starting materials for production of light heating and diesel oils and of heavy heating oil. The compounds present have boiling points of 180 to 360° C. They are preferably predominantly saturated compounds which can be converted in a thermal steamcracking operation. In addition, it is also possible to use fractions obtained by known distillative separation processes and corresponding residues, but also the use of fractions derived therefrom, for example by hydrogenation (hydrotreating) or hydrocracking. Examples are light, heavy and vacuum gas oil (atmospheric gas oil, AGO, or vacuum gas oil, VGO), and also mixtures and/or residues treated by the hydrogenation processes mentioned (hydrotreated vacuum gas oil, HVGO, hydrocracker residue, HCR, or unconverted oil, UCO).

Very particularly advantageous fresh feeds for the first hydrocarbon feed are liquid hydrocarbons. More particularly, the fresh feeds used are natural gas condensates and/or crude oil fractions and/or mixtures derived therefrom.

Advantageously, the invention thus encompasses the use of hydrocarbon mixtures having a boiling range of up to 600° C. as the first hydrocarbon feed as fresh feed for the first hydrocarbon feed. Within this overall range, it is also possible to use hydrocarbon mixtures having different boiling ranges, for example having boiling ranges of up to 360° C. or of up to 240° C. The reaction conditions in the cracking furnace are matched here to the hydrocarbon mixtures used in each case.

For instance, the invention can, however, also advantageously be used with any other desired fresh feeds having comparable properties, for example biogenic or/and synthetic hydrocarbons.

BRIEF DESCRIPTION OF THE DRAWING

The process according to the invention in a particularly advantageous configuration is to be elucidated in detail with reference to the process flow diagrams which show the essential process steps in schematic form. For better understanding, the known process is first illustrated with reference to FIG. 1.

Figure 1:
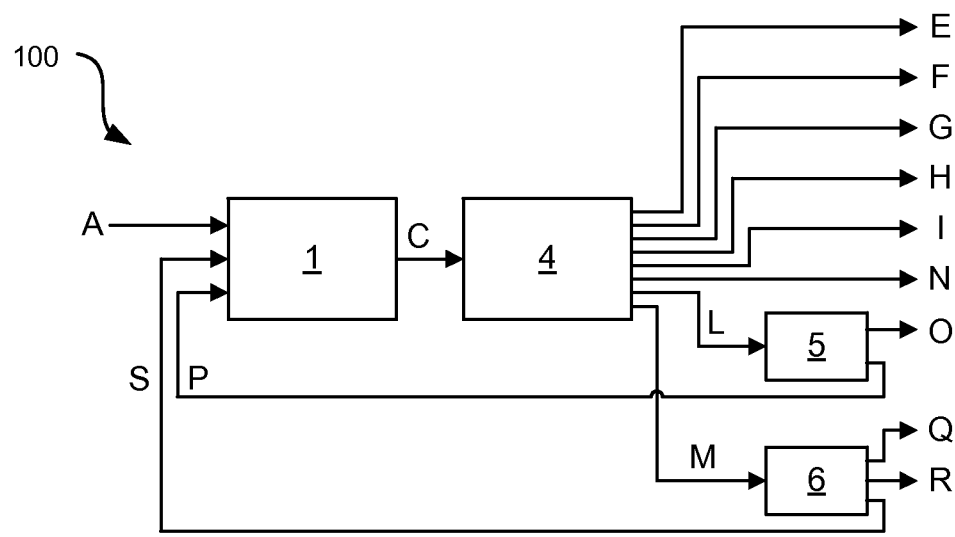
FIG. 1 shows a schematic view of a known method for olefin production.

The schematic process flow diagram 100 of FIG. 1 for the known process includes a cracking furnace 1 into which the fresh feed A (for example naphtha) and the recycled fractions S and P as hydrocarbon feeds are conducted. In the cracking furnace 1, the hydrocarbon feed is heated and converted in convection and radiation zones. Steam is added to the cracking furnace, usually 0.5 to 1 kg of process steam per kg of hydrocarbon. A product stream C emerges from the cracking furnace 1, and this is also referred to as the cracking product stream directly at the exit from the cracking furnace. On exit from the cracking furnace, this cracking product stream has a temperature normally between 840° C. and 900° C. The ratio of propylene to ethylene is generally 0.35 to 0.6 kg/kg. After a first quench (not shown), the product stream is processed in a processing unit 4. From the processing unit, the following fractions are obtained as essential product fractions E to N: hydrogen E, waste liquor F, methane G, ethylene H, propylene I, gaseous hydrocarbons L having a carbon number of 4, pyrolysis gasoline M and pyrolysis oil N. The gaseous hydrocarbons L having a hydrocarbon number of 4 are treated further in a C4 processing unit 5, which is utilized for the processing of hydrocarbons having a carbon number of 4. Such a C4 processing unit 5 treats the fraction having a carbon number of 4 further in such a way that butadiene O can be removed. The other hydrocarbons having a carbon number of 4 constitute a fraction P which is recycled into the cracking furnace 1. The pyrolysis gasoline M comprising hydrocarbons having a carbon number of 5 or more is processed further in a pyrolysis gasoline processing unit 6, and aromatics Q and hydrocarbons R having a carbon number of, for example, more than 9 are removed. The other hydrocarbons having a carbon number of 5 or more are recycled as fraction S into the cracking furnace 1. The processing unit 4, and also the C4 processing unit 5 and the pyrolysis gasoline processing unit 6, comprise customary units for further processing of the product stream or of the product fractions, which serve to execute various process steps, for example compression, condensation and cooling, drying, distillation and fractionation, extraction and hydrogenation. The process steps are customary in olefin plants are are known to those skilled in the art.

Figure 2:
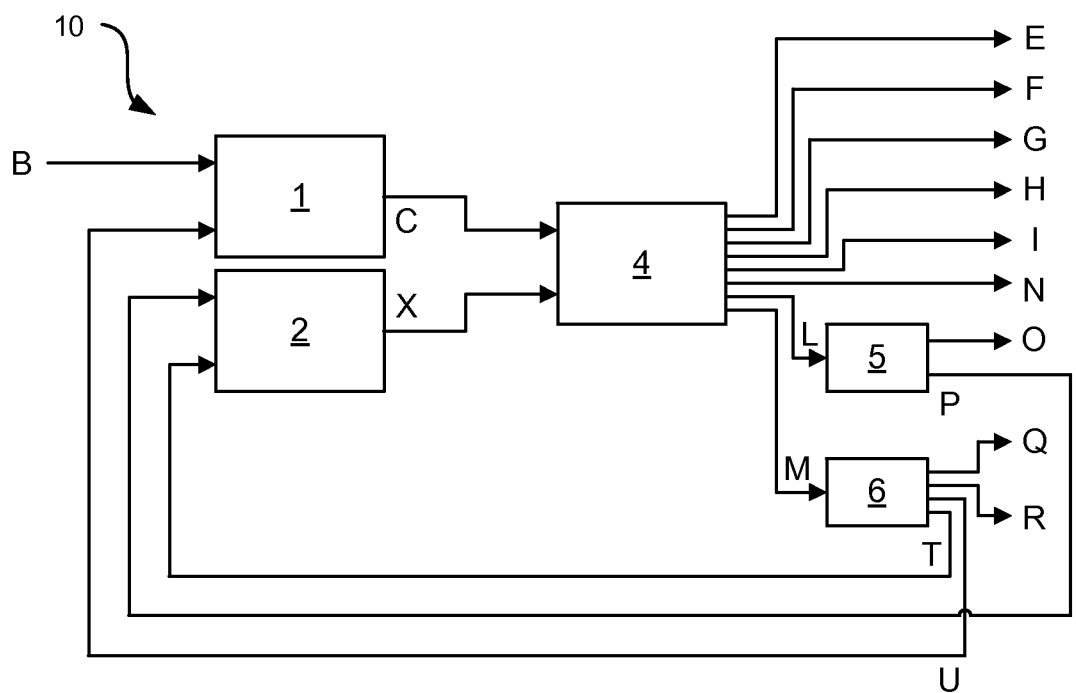
FIG. 2 shows a schematic view of the essential steps of the process according to the invention in a particularly advantageous configuration.

The schematic process flow diagram 10 of FIG. 2 then shows the process according to the invention in a particularly advantageous configuration, and the essential process steps thereof. In addition to the cracking furnace 1, into which the fresh feed B (for example naphtha) and the recycled fraction U are conducted as the first hydrocarbon feed, a second cracking furnace 2 is present here. As the second hydrocarbon feed, the fractions P and T are conducted into the second cracking furnace 2. In turn, the cracking product stream C having the abovementioned properties emerges from the first cracking furnace 1. The cracking product stream X emerges from the second cracking furnace 2. The cracking product stream X is at a temperature advantageously between 700° C. and 800° C. The ratio of propylene to ethylene therein is advantageously between 0.7 and 1.5 kg/kg. The product streams C and X are processed further in the processing unit 4 and combined at a suitable point to give a common product stream. The processes for further treatment and processing in the processing unit 4 are known and have just been described. Thus, the processing unit 4 also leads, as just described, to the product fractions E to N. The product fractions L and M too, as just described, are treated further in the specific processing units 5 and 6. In contrast to the process described in FIG. 1, however, the fraction P comprising hydrocarbons having a carbon number of 4 is recycled not into the cracking furnace 1 but into the second cracking furnace 2. In the pyrolysis gasoline processing unit 6, as well as the abovementioned fractions Q and R, the fractions T and U are obtained. The fraction T comprising hydrocarbons having a carbon number of 5 is recycled into the second cracking furnace 2, while the fraction U comprising hydrocarbons having a carbon number of 6 or more, especially between 6 and 9, is recycled into the first cracking furnace 1.

Figure 3:
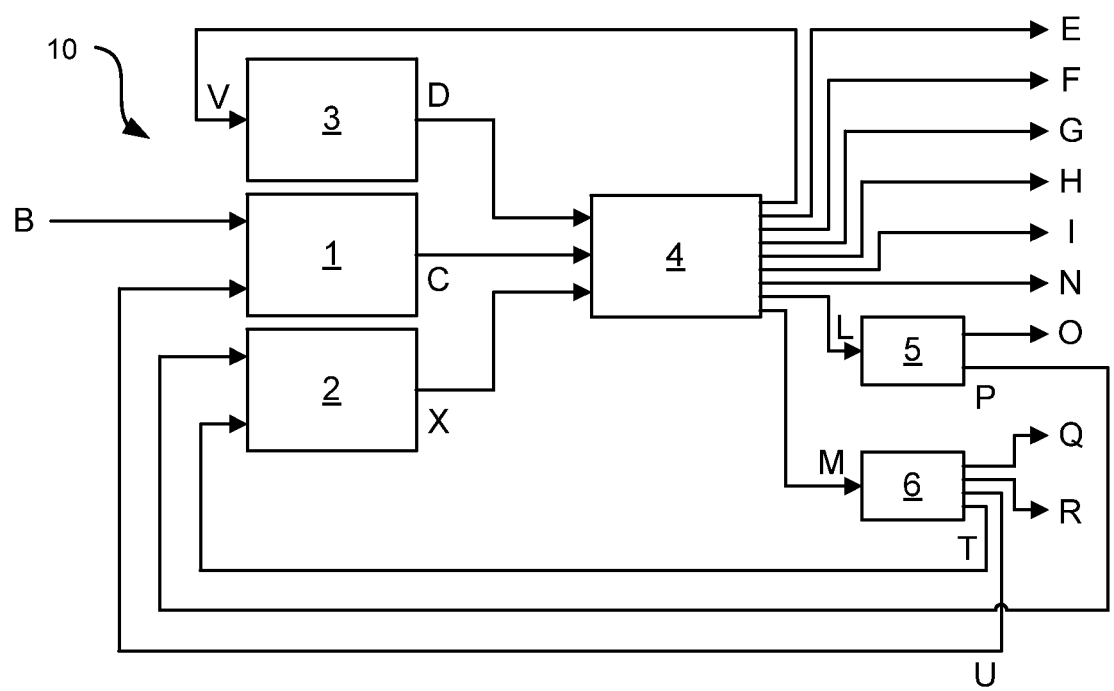
FIG. 3 shows, likewise in schematic form, the essential steps of a particularly advantageous configuration of the invention. In the figures, corresponding elements bear identical reference numerals.

A particularly advantageous configuration of the invention includes FIG. 3. FIG. 3 has the same schematic process flow diagram as also shown in FIG. 2. This is supplemented by a cracking furnace 3 for gaseous feed, into which a fraction V is conducted as feed. The fraction V comprises saturated gaseous hydrocarbons having a carbon number of 2 or 3, which are likewise obtained in the processing unit 4.

LIST OF REFERENCE NUMERALS 1 cracking furnace (normal cracking conditions)
2 cracking furnace (mild cracking conditions)
3 cracking furnace for gaseous feed
4 processing unit
5 C4 processing unit
6 pyrolysis gasoline processing unit
10 schematic process flow diagram for a known process
100 schematic process flow diagram for the process according to the invention in a particularly advantageous configuration
A, B fresh feed
C, D, X product streams
E-V product fractions

The invention claimed is:

1. A process for converting hydrocarbon feeds by thermal steamcracking to an olefin-containing product stream comprising at least ethylene and propylene, with at least partial conversion of a first hydrocarbon feed in at least one first cracking furnace (1) and of a second hydrocarbon feed in at least one second cracking furnace (2), characterized in that the second hydrocarbon feed comprises predominantly hydrocarbons having a carbon number of 5 or/and 4 and consists for the most part of one or more recycled fractions (P, T) which are obtained from the product stream, the second hydrocarbon being converted in the second cracking furnace (2) with cracking conditions that lead to a ratio of propylene to ethylene of 0.85 to 1.6 kg/kg, the first hydrocarbon feed being supplied with at least one fraction (U) which has been separated from the product stream and is recycled, comprising predominantly hydrocarbons having a carbon number of at least 6, the first hydrocarbon feed being converted in the first cracking furnace (1) with cracking conditions that lead to a ratio of propylene to ethylene of 0.25 to 0.85 at the cracking furnace outlet, and the value for the ratio of propylene to ethylene for the second hydrocarbon feed being above the value for the ratio of propylene to ethylene for the first hydrocarbon feed.

2. The process as claimed in claim 1, characterized in that the second hydrocarbon consists exclusively of one or more recycled fractions (P, T).

3. The process as claimed in claim 1, characterized in that the hydrocarbons having a carbon number of 5 present in the second hydrocarbon feed are predominantly saturated hydrocarbons.

4. The process as claimed in claim 1, characterized in that the second hydrocarbon is substantially free of diolefins.

5. The process as claimed in claim 1, characterized in that the second hydrocarbon feed comprises predominantly saturated hydrocarbons.

6. The process as claimed in claim 1, characterized in that the second hydrocarbon is converted in the second cracking furnace (2) with cracking conditions that lead to a ratio of propylene to ethylene of up to 1.2 kg/kg, at the cracking furnace outlet.

7. The process as claimed in claim 1, characterized in that the first hydrocarbon feed is converted in the first cracking furnace (1) with cracking conditions that lead to a ratio of propylene to ethylene of 0.3 to 0.75 kg/kg, preferably of 0.4 to 0.65 kg/kg, at the cracking furnace outlet.

8. The process as claimed in claim 1, in which the values for the ratio of propylene to ethylene for the first and second hydrocarbons differ by at least 0.1 kg/kg, preferably by at least 0.15 kg/kg, more preferably by at least 0.2 kg/kg.

9. The process as claimed in claim 1, in which the cracking furnace exit temperature for the conversion in the second cracking furnace (2) is between 680° C. and 820° C., preferably between 700° C. and 800° C. and further preferably between 710° C. and 780° C. and more preferably between 720° C. and 760° C., and the cracking furnace exit temperature for the conversion in the first cracking furnace (1) is between 800° C. and 1000° C., preferably between 820° C. and 950° C. and more preferably between 840° C. and 900° C., the cracking furnace exit temperature of the first cracking furnace (1) being above that of the second cracking furnace (2).

10. The process as claimed in claim 9, in which the cracking furnace exit temperature for the conversion in the first cracking furnace (1) is at least 10° C. above, preferably at least 15° C. above, more preferably at least 20° C. above, the cracking furnace exit temperature for the conversion in the second cracking furnace (2).

11. The process as claimed in claim 1, in which 0.3 to 1.5 kg of steam per kg of hydrocarbon feed is used in the first cracking furnace (1), and 0.15 to 0.8 kg of steam per kg of hydrocarbon feed in the second cracking furnace (2).

12. The process as claimed in claim 1, in which at least one fraction (V) comprising predominantly hydrocarbons having a carbon number of 2 or 3 is obtained from the product stream and at least partly converted in a cracking furnace (3) for gaseous feed.

13. The process as claimed in claim 1, characterized in that the fresh feed (B) used for the first hydrocarbon feed comprises natural gas condensates and/or crude oil fractions, especially naphtha, and/or synthetic and/or biogenic hydrocarbons and/or mixtures derived therefrom.

* * * * *